United States Patent [19]

Larkin et al.

[11] Patent Number: 5,085,643
[45] Date of Patent: Feb. 4, 1992

[54] SYRINGE, ADAPTOR, AND CHECK VALVE COMBINATION FOR PARENTERAL INFUSER

[75] Inventors: Mark E. Larkin, Lindenhurst; John E. Ogden, Libertyville; Dale V. Moeller, Wadsworth, all of Ill.

[73] Assignee: Abbott Laboratories, Abbott Park, Ill.

[21] Appl. No.: 360,965

[22] Filed: Jun. 2, 1989

[51] Int. Cl.⁵ .............................................. A61M 1/00
[52] U.S. Cl. .................................. 604/152; 604/208; 604/247; 604/246
[58] Field of Search ........................... 604/65-67, 604/131, 151, 152, 154, 208, 246-247

[56] References Cited

U.S. PATENT DOCUMENTS

| | | | |
|---|---|---|---|
| 4,310,017 | 1/1982 | Raines | 604/247 |
| 4,627,839 | 12/1986 | Young | 604/154 |
| 4,828,551 | 5/1989 | Gertler et al. | 604/208 |

Primary Examiner—Stephen C. Pellegrino
Assistant Examiner—Michael Rafa
Attorney, Agent, or Firm—A. Nicholas Trausch

[57] ABSTRACT

A combination comprising a syringe, an adaptor, a check valve, and associated connectors for an intravenous infuser for patient-controlled analgesia. The infuser comprises a cradle adapted to receive an annular or disc-shaped element fitting into the cradle and a switch adapted to disable the infuser unless such an element is fitted into the cradle. The syringe comprises a vial, a plunger arranged within the vial for relative movement of the plunger and the vial, a tubular needle extending through an axial hole of the plunger, and a flange mounted around the needle and spaced from the plunger but too small to fit into the cradle. An adaptor having an outer rim adapted to fit over the flange and into the cradle and a check valve mounted operatively in the adaptor are connected by tubular connectors to the flange. The check valve allows an infusible liquid to flow from a chamber within the vial, through the tubular needle, and through the check valve, but not oppositely.

5 Claims, 3 Drawing Sheets

SYRINGE, ADAPTOR, AND CHECK VALVE COMBINATION FOR PARENTERAL INFUSER

BACKGROUND OF THE INVENTION

This invention pertains to improved components including a syringe and a check valve for a parenteral infuser, particularly but not exclusively an intravenous infuser. The infuser is preferably utilized for the administration of patient-controlled analgesia.

As manufactured by or for Abbott Laboratories, Hospital Products Division, North Chicago, Ill. 60064, and sold under its trademark "LifeCare", an intravenous infuser for patient-controlled analgesia ("PCA") comprises a pump, which is arranged to deliver individual, controlled doses of an infusible liquid containing an analgesic agent or agents, at patient-controlled intervals, for intravenous infusion into a patient. The patient is provided with a remote actuator or button, which he or she can press to actuate the pump. The pump is controlled so that it can be so actuated only if necessary conditions have been satisfied, e.g., only if a sufficient interval has passed since a prior dose was administered to the patient.

In the intravenous infuser described in the preceding paragraph, the pump, whenever so actuated, operates a syringe, which includes a vial and a plunger arranged within the vial for relative movement of the plunger and the vial along an axis of the vial. In use, the plunger is stationary, whereas the vial is movable. The syringe also includes a tubular needle, which extends through the plunger, and which conducts the infusible liquid to a check valve allowing the infusible liquid to flow, via a flexible tube, toward a site for intravenous administration to the patient. The check valve does not allow the infusible liquid, or any other liquid, to flow into the vial. The infusible liquid is caused to flow, as permitted by the check valve, upon relative movement of the plunger and the vial so as to shorten the chamber holding the infusible liquid. The infusible liquid is retained in the chamber, otherwise, by relative pressures on the infusible liquid.

Moreover, the syringe is provided with an annular flange, which fits into a cradle mounted on the pump. The pump is provided with a switch, which disables the intravenous infuser unless such a flange or an equivalent element is fitted into the cradle. The check valve is connected to the annular flange. However, since standard connectors, e.g., Luer connectors, are used not only to connect the check valve to the annular flange, as provided on the syringe, but also to connect the flexible tube to the check valve, it is possible for the check valve to be inadvertently or deliberately omitted and for the flexible tube to be directly connected to the annular flange. Without the check valve, if the vial of the syringe were to be accidentally cracked, siphoning could occur, which would be highly undesirable.

SUMMARY OF THE INVENTION

This invention provides a novel combination comprising a syringe, an adaptor, a check valve, and associated connectors for a parenteral infuser. The infuser is preferably utilized for the administration of patient-controlled analgesia. The parenteral infuser comprises a cradle adapted to receive an annular or disc-shaped element fitting into the cradle and a switch adapted to disable the parenteral infuser unless such an element is fitted into the cradle. The "LifeCare" PCA infuser described above exemplifies such an infuser.

The syringe, which has a chamber adapted to hold an infusible liquid, includes a vial having a tubular wall with a closed end and an open end. The vial encloses the chamber except at one end opposite the closed end of the vial. The syringe also includes a plunger arranged within the vial for relative movement of the plunger and the vial along an axis of the vial. The plunger closes the chamber liquid-tightly except for an axial hole of the plunger. The syringe further includes a tubular needle extending axially through the open end of the vial, and liquid-tightly through the axial hole of the plunger, and a flange mounted around the tubular needle in fixed, spaced relation to the plunger. The flange is too small to fit into the cradle.

A first set of tubular connectors adapted to be releasable connected to each other is provided. A first connector of the first set is attached to the flange so as to communicate with the tubular needle. The first set also includes a second connector discussed below.

The adaptor, which preferably is funnel-shaped, has an outer rim, which preferably is annular, and which is adapted to fit into the cradle. The check valve, which is attached at a given end to the second connector of the first set of tubular connectors, is mounted operatively in the adaptor so as to allow the infusible liquid to flow from the chamber, through the tubular needle, and through the check valve, but not oppositely, when the adapter is fitted over the flange of the syringe and into the cradle and the first and second connectors of the first set of tubular connectors are connected to each other.

A second set of tubular connectors adapted to be releasably connected to each other is provided. A first connector of the second set is attached to the opposite end of check valve and extended from the adaptor. A second connector of the second set is adapted to connect a tube leading toward a site for parenteral infusion of a patient.

Various components of the combination noted above may be advantageously molded from a polymer suitable for usage in a hospital and for contact with the infusible liquid, e.g., a polycarbonate or acrylic polymer. Such polymers are well known. Desirably, if molded from one such polymer, the adaptor, the check valve, and the connectors attached to the check valve may be ultrasonically welded or solvent bonded into a unitary assembly.

These and other objects, features, and advantages of this invention are evident from the following description of a preferred embodiment of this invention with reference to the accompanying drawings.

DETAILED DESCRIPTION OF PREFERRED EMBODIMENT

Figure 1:
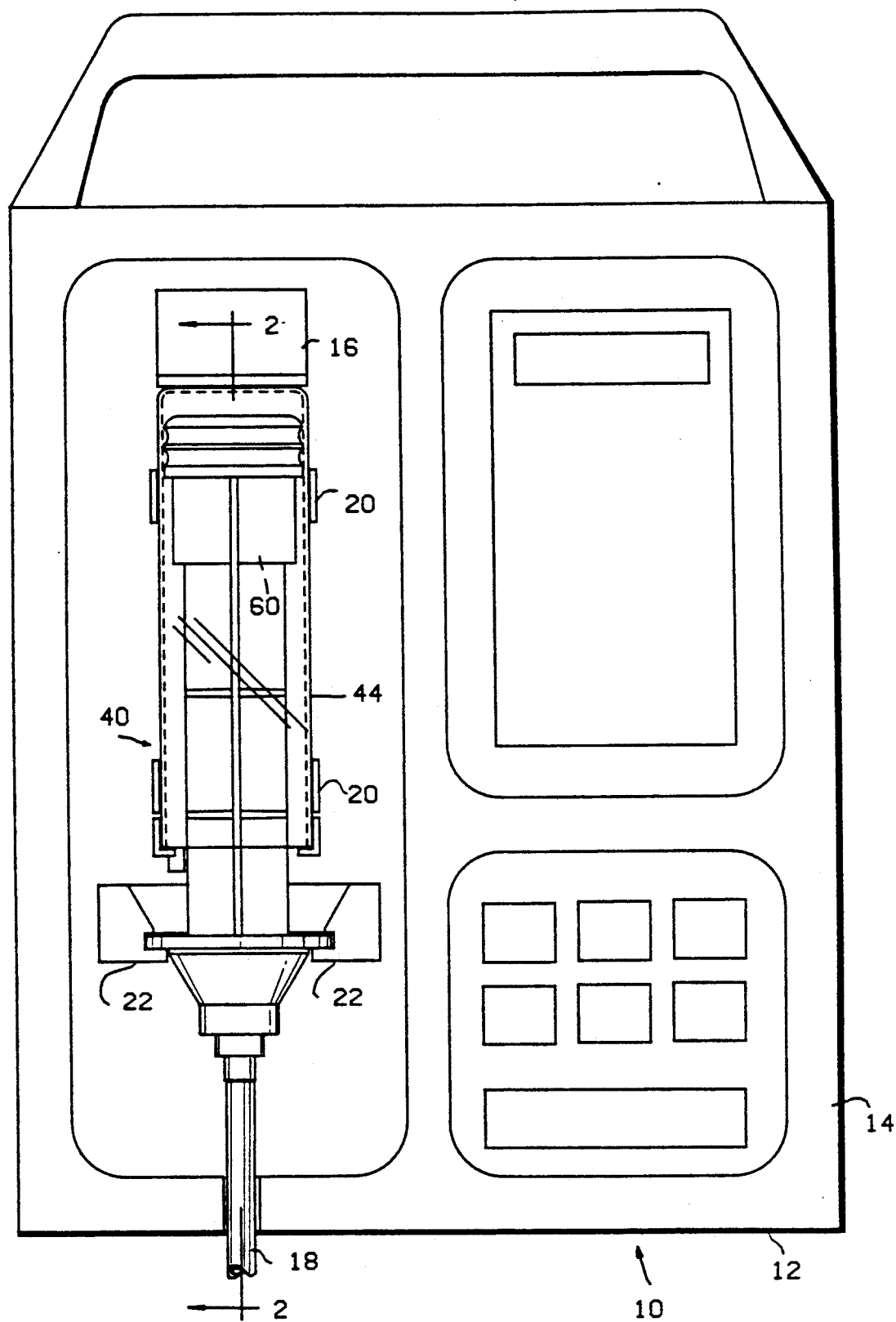
FIG. 1 is an elevational view of principal components of an intravenous infuser including a syringe, adaptor, and check valve combination constituting a preferred embodiment of this invention.
Figure 2:
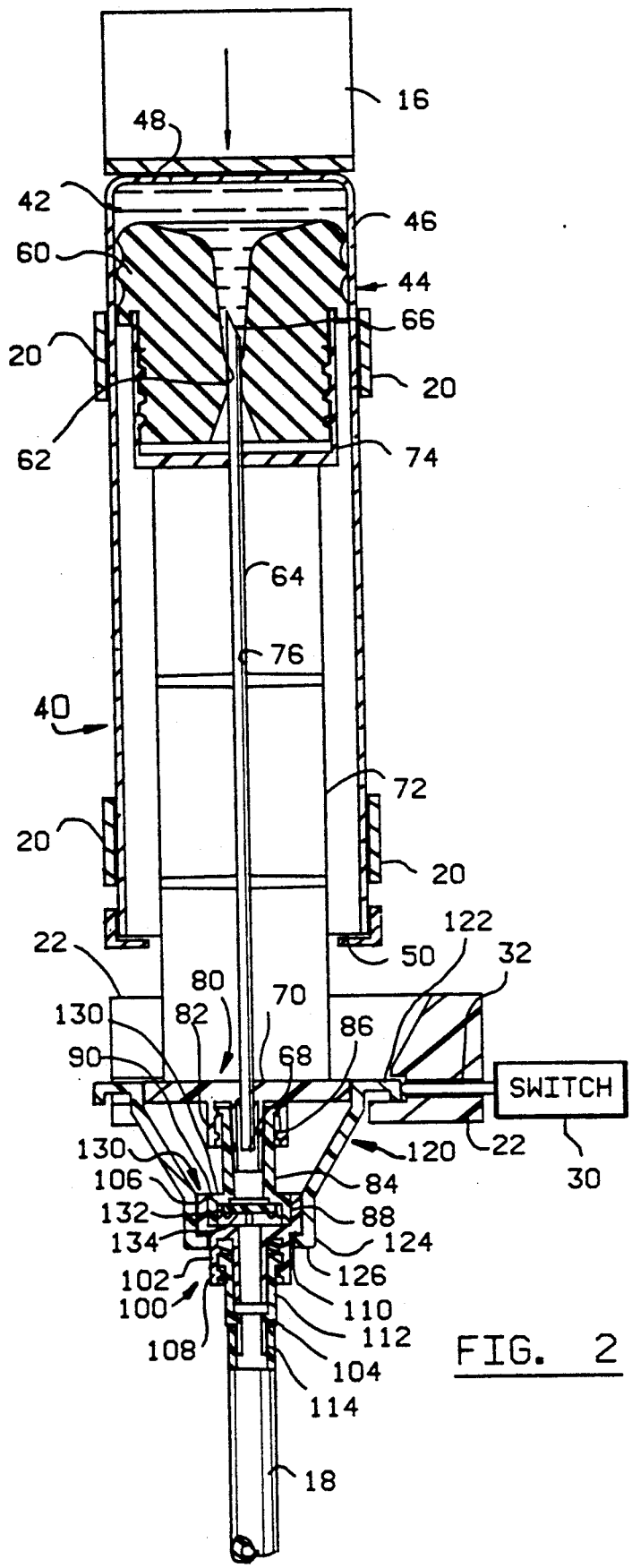
FIG. 2 is an enlarged sectional view of the syringe, adaptor, and check valve combination, as taken along line 2——2 of FIG. 1 in a direction indicated by arrows.
Figure 3:
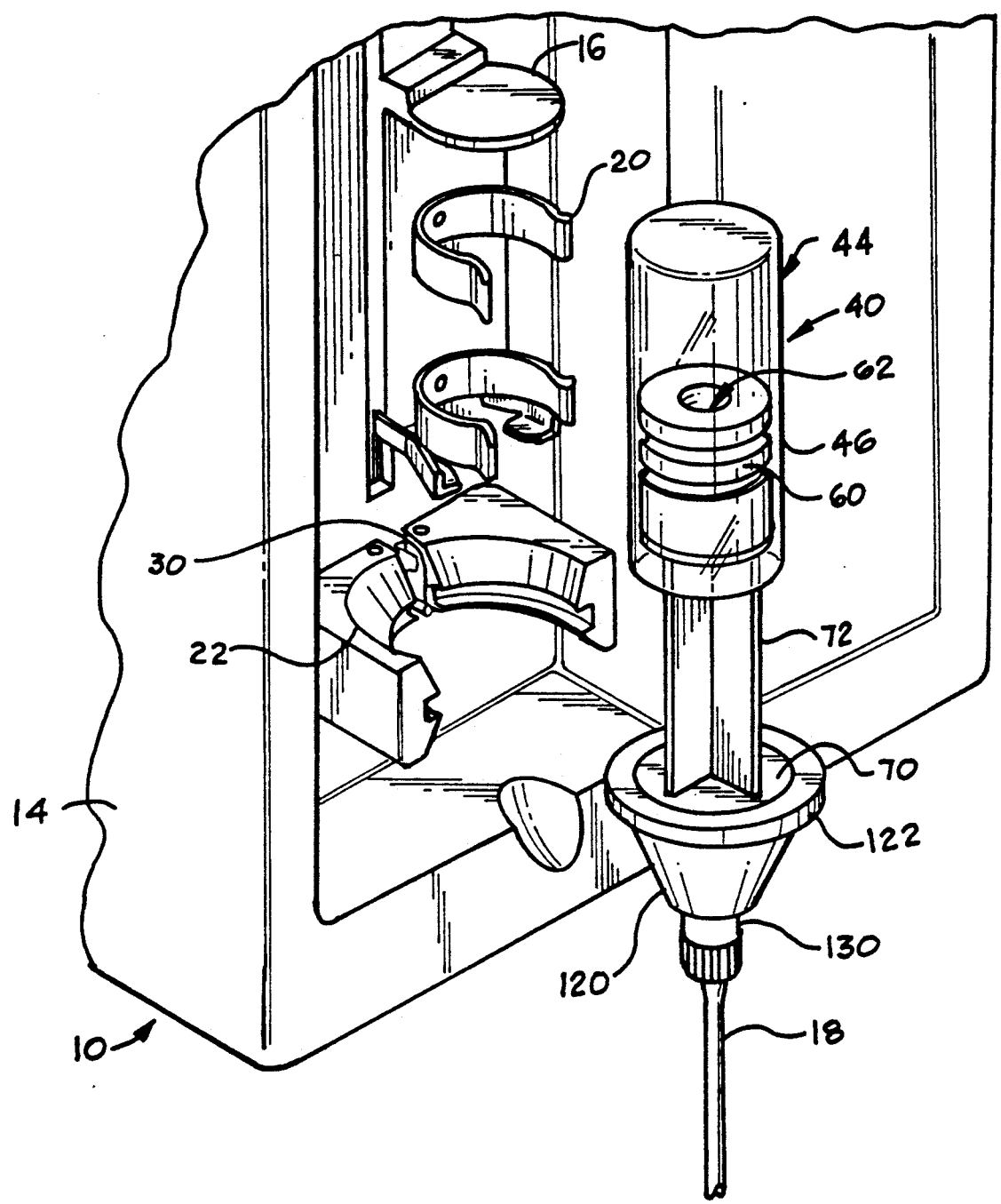
FIG. 3 is a partial perspective view of an unassembled infuser and syringe of the present invention.

As shown in FIG. 1, FIG. 2, and FIG. 3, an intravenous infuser 10 for patient-controlled analgesia comprises a pump 12 in a case 14, which also encases various displays and settable controls outside the scope of this invention. These displays and settable controls enable medical personnel to control such parameters as dosage volume and lockout interval, i.e., minimum interval between successive doses, and to monitor various functions of the intravenous infuser 10.

A patient for whom patient-controlled analgesia is prescribed is provided with a remote actuator or button (not shown) which is connected operatively to the intravenous infuser 10, and which he or she can press to actuate the pump 12 if necessary conditions have been satisfied, e.g., if a sufficient interval has passed since a prior dose was administered to the patient. When actuated, the pump 12 imparts a controlled amount of downward displacement to a driver 16, which actuates a syringe described below to cause the syringe to deliver a controlled dose of the infusible liquid, via a check valve described below, and via a flexible tube 18 leading toward a site (not shown) for intravenous administration of the controlled dose of the infusible liquid to the patient. Downward displacement of the driver 16 is indicated by an arrow in FIG. 2. A clip 20, which is connected to the driver 16 so as to be conjointly movable with the driver 16, is adapted to hold the syringe in proper position relative to the driver 16.

The intravenous infuser 10 is equipped with a cradle 22, which is mounted on an outer face of the case 14. The cradle 22, which is comprised of two hemiconical halves is C-shaped and made of a rigid material that is pivotably mounted with a spring return (not shown) embedded therein, is adapted to receive an annular or disc-shaped element of suitable dimensions enabling the element to fit into the cradle 22 with a snap-fit. The intravenous infuser 10 also is equipped with a switch 30, which is shown semi-diagrammatically in FIG. 2 and FIG. 3. The switch 30 has an actuator 32, which is disposed so as to be operatively engaged by such an element fitted into the cradle 22, and is adapted to disable the intravenous infuser 10 unless such an element is fitted into the cradle 22 so as to actuate the switch 30 via the actuator 32. In the "LifeCare" PCA infuser described above, such a cradle, such a switch, and such a syringe are provided, and the syringe is provided with an annular flange constituting such an element, which can be thus fitted into the cradle.

The intravenous infuser 10 further comprises a syringe 40, as mentioned above, which has a chamber 42 adapted to hold a useful quantity of the infusible liquid, e.g., enough of the infusible liquid to provide at least several of the controlled doses. The syringe 40 includes a vial 44, which preferably is made of transparent glass. The vial 44 has a tubular wall 46 extending vertically with a closed, upper end 48 and an open, lower end 50, as well as a vertical axis. The vial 44 encloses the chamber 42 except at the lower end of the chamber 42. The lower end of the chamber 42 is opposite the closed, upper end 48 of the chamber 42. The syringe also includes a plunger 60, which may be advantageously molded of a suitable, elastomeric polymer, e.g., synthetic rubber. The plunger 60 is arranged within the vial 44 for relative movement of the plunger 60 and the vial 44 along the vertical axis of the vial 44. As shown, the plunger 60 is stationary, whereas the vial 44 is movable. The vial 44 is engaged at its closed, upper end 48 by the driver 16, which is displaced downwardly by a controlled displacement, when the pump 12 is actuated, so as to shorten the chamber 42 in an axial direction and thus to cause the syringe 40 to deliver a controlled dose of the infusible liquid. As shown, the tubular wall 46 of the vial 44 fits into the clip 20, which is adapted to hold the vial 44 in proper position relative to the driver 16.

The plunger 60, which has an axial hole 62, closes the chamber 42 liquid-tightly at the lower end of the chamber 42 except for the axial hole 62. A tubular needle 64 having a sharp, upper end 66 and a blunt, lower end 68 extends axially through the open end 50 of the vial 44, and liquid-tightly through the axial hole 62 of the plunger 60, so that the sharp, upper end 66 communicates with the chamber 42. The sharp, upper end 66 of the tubular needle 64 facilitates assembly of the plunger 60 and the tubular needle 64. The tubular needle 64 is held in the axial hole 62 with an interference fit.

An annular flange 70 is mounted around the tubular needle 64, at a location near the blunt, lower end 68, in fixed, spaced relation to the plunger 60. A columnar spacer 72, which is cross-shaped in cross-section, is mounted rigidly to an upper cup 74 receiving a lower portion of the plunger 60 with an interference fit, which is enhanced by complementary formations on the upper cup 74 and on the lower portion of the plunger 60, as shown in FIG. 2. The columnar spacer 72, which has an elongate hole 76 accommodating the tubular needle 64, is mounted rigidly to the annular flange 70 to retain the annular flange 70 in fixed, spaced relation to the plunger 60. The annular flange 70, the columnar spacer 72, and the upper cup 74 may be advantageously molded, as one part or plural parts, from a suitable polymer and, if molded as plural parts, may be ultrasonically welded or solvent bonded into a unitary structure. The annular flange 70 is too small to fit into the cradle 22 so as to actuate the switch 30 via the actuator 32.

A first set of 80 of tubular connectors is provided, namely, a first, female connector 82 and a second, male connector 84. Each of the connectors 82, 84, may be advantageously molded from a suitable polymer. The first, female connector 82, which has radially spaced, inner and outer, tubular portions, is integral with and may be advantageously molded in one piece with the annular flange 70 to depend axially from the annular flange 70. The second, male connector 84 has an upper, tubular portion 86 and a lower tubular portion 88, which is joined to the upper, tubular portion 86 to form an annular portion 90. The tubular portions of the first, female connector 82 and the upper, tubular portion 86 of the second, male connector 84 have complementary formations conforming to standard Luer connectors and thus are adapted to be releasably connected to each other, as shown, in a manner typical of such Luer connectors.

A second set 100 of tubular connectors is provided, namely, a first, female connector 102 and a second, male connector 104. Each of the connectors 102, 104 may be advantageously molded from a suitable polymer. The first, female connector 102 has an upper, tubular portion 106 and lower, radially spaced, inner and outer, tubular portions 108, which are joined to the upper, tubular portion 106 to form an annular portion 110. The second, male connector 104 has an upper, tubular portion 112 and a lower, tubular portion 114. The lower, tubular portions 108 of the first, female connector 102 and the upper, tubular portion 112 of the second, male connector 104 have complementary formations conforming to standard Luer connectors and thus are adapted to be releasably connected to each other, as shown, in a manner typical of such Luer connectors. The lower, tubular portion 114 of the second, male connector 104 is adapted to connect the flexible tube 18, which can be slightly expanded so as to fit liquid-tightly over the lower, tubular portion 114.

The intraveneous infuser 10 also comprises an adaptor 120, which is funnel-shaped, and which may be advantageously molded from a suitable polymer. The adaptor 120 has an outer, upper, annular rim 122, which is adapted to fit over the annular flange 70, and which is adapted to fit into the cradle 22 so as to actuate the switch 30 via the actuator 32. The adaptor 120 has a lower, tubular portion 124 terminating in an inner, lower, annular rim 126.

The intravenous infuser 10 further comprises a check valve 130 mounted operatively in the adaptor 120. The check valve 130 includes the lower, tubular portion 88 of the male connector 84 of the first set 80 of the tubular connectors, the annular portion 90 of the connector 84, the upper, tubular portion 106 of the first, female connector 102 of the second set 100 of tubular connectors, and a movable flexible disc 132. The movable disc 132, which has a diameter less than the inner diameter of the lower, tubular portion 88 of the connector 84, has a flat, upper surface, and a lower surface provided with a plurality of depending nubs 134, two of which are shown in FIG. 2.

The first, female connector 102 of the second set 100 of tubular connectors is mounted rigidly, e.g., welded ultrasonically or solvent bonded if molded from a suitable polymer, to the adaptor 120 so that the upper, tubular portion 106 of the connector 102 is mounted within the lower, tubular portion 124 of the adaptor 120, so that the annular portion 110 of the connector 102 is seated on the annular rim 126 of the adaptor 120, and so that the lower, tubular portions 108 of the connector 102 extend axially and downwardly from the adaptor 120. The second, female connector 84 of the first set 80 of tubular connectors is mounted rigidly, e.g., welded ultrasonically or solvent bonded if molded from a suitable polymer, to the connector 102 and assembled with the movable disc 132 of the check valve 130 so that the lower, tubular portion 88 of the connector 84 surrounds the movable disc 132 and is mounted within the upper, tubular portion 106 of the connector 102, and so that the annular portion 90 of the connector 84 is seated on the annular portion 110 of the connector 102. Consequently, the movable disc 132 is retained within the lower, tubular portion B8 of the connector 84 and is permitted movement over a limited range between the annular portion 110 of the connector 102 and the annular portion 90 of the connector 84.

In the uppermost position of the movable disc 132 within its limited range of movement, the flat, upper surface of the disc 132 bears against the annular portion 90 of the connector 84 so as to prevent the infusible liquid, or any other liquid, from flowing upwardly into the blunt, lower end 68 of the tubular needle 64. In the lowermost position of the movable disc 132 within the same range, the nubs 134 projecting from the lower surface of the movable disc 132 bear against and elevate the lower surface of the movable disc 132 from the annular portion 110 of the connector 102. Since the diameter of the movable disc 132 is less than the inner diameter of the lower, tubular portion 88 of the connector 84, the check valve 130 via the movable disc 132 allows the infusible liquid to flow from the chamber 42, through the tubular needle 64, and through the check valve 130, but not oppositely. Thus, if the vial 44 should be accidentally cracked, the check valve 130 would prevent siphoning.

The syringe, adaptor, check valve, and associated connectors described above are combined in a novel combination constituting the preferred embodiment of this invention. Various changes may be made thereto without departing from the scope and spirit of this invention.

We claim:

1. For use in a parenteral infuser comprising a cradle adapted to receive an annular or disc-shaped element fitting into the cradle and a switch adapted to disable the parenteral infuser unless such an element is fitted into the cradle, a combination comprising:
   a. a syringe having a chamber adapted to hold an infusible liquid and including
      1. a vial having a tubular wall with a closed end and an open end, having a longitudinal axis, and enclosing the chamber except at one end opposite the closed end of the vial,
      2. a plunger arranged within the vial, in liquid-tight relation to the tubular wall of the vial, for relative movement of the plunger and the vial along the axis of the vial, the plunger having an axial hole and closing the chamber liquid-tightly at the end opposite the closed end of the vial except at the axial hole,
      3. a tubular needle extending axially through the open end of the vial, and liquid-tightly through the axial hole of the plunger, and
      4. a flange mounted around the tubular needle in fixed, spaced relation to the plunger, the flange being too small to fit into the cradle,
   b. a first set of male and female tubular connectors adapted to be releasably connected to each other, the first set of tubular connectors including a first connector axially attached to the flange of the syringe so as to communicate with the tubular needle and a second connector;
   c. an adaptor having an upper portion including an outer rim adapted to fit into the cradle and an inner rim adapted to fit over the flange of the syringe and a lower tubular portion axially spaced from the upper portion;
   d. a check valve having a fluid inlet, a fluid outlet, and means for allowing fluid to flow only from the inlet to the outlet, said valve adapted to fit in the tubular portion of the adaptor and fluidly connected to the first connector at the fluid inlet by the second connector of the first set of tubular connectors so as to allow the infusible liquid to flow from the chamber, through the tubular needle, and through the check valve, but not oppositely, when the adaptor is fitted over the flange of the syringe and into the cradle and the first and second connectors of the first set of tubular connectors are connected to each other; and
   e. a second set of tubular connectors adapted to be releasably connected to each other, the second set of tubular connectors including a first connector attached to the fluid outlet of the check valve and axially extended from the tubular portion of the adaptor and a second connector adapted to connect a tube leading toward a site for parenteral infusion of a patient.

2. The combination of claim 1 wherein the upper portion of the adaptor is annular.

3. The combination of claim 2 wherein the flange of the syringe is circular.

4. The combination of claim 1 wherein the adaptor is funnel-shaped.

5. The combination of claim 4 wherein the upper portion of the adaptor is annular and the flange of the syringe is circular.

* * * * *

UNITED STATES PATENT AND TRADEMARK OFFICE
CERTIFICATE OF CORRECTION

PATENT NO. : 5,085,643
DATED : February 4, 1992
INVENTOR(S) : Mark E. Larkin; John E. Ogden; Dale V. Moeller It is certified that error appears in the above-identified patent and that said Letters Patent is hereby corrected as shown below:

Column 5, Line 53; Replace "B8" with --88--

Signed and Sealed this

Eighth Day of June, 1993

Attest:

MICHAEL K. KIRK

Attesting Officer

Acting Commissioner of Patents and Trademarks